US007507407B2

(12) United States Patent
Benz et al.

(10) Patent No.: US 7,507,407 B2
(45) Date of Patent: *Mar. 24, 2009

(54) IMMUNOLIPOSOMES THAT OPTIMIZE INTERNATIONALIZATION INTO TARGET CELLS

(75) Inventors: Christopher C. Benz, Novato, CA (US); Demetrios P. Papahadjopoulos, San Francisco, CA (US); John W. Park, San Francisco, CA (US); Keelung Hong, San Francisco, CA (US); Dmitri Kirpotin, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/546,781

(22) Filed: Oct. 11, 2006

(65) Prior Publication Data
US 2007/0031484 A1 Feb. 8, 2007

Related U.S. Application Data

(63) Continuation of application No. 09/797,544, filed on Feb. 28, 2001, now Pat. No. 7,135,177, which is a continuation of application No. 08/634,197, filed on Apr. 18, 1996, now Pat. No. 6,214,388, which is a continuation-in-part of application No. 08/336,860, filed on Nov. 9, 1994, now abandoned.

(51) Int. Cl.
A61K 39/395 (2006.01)
(52) U.S. Cl. ................................. 424/143.1
(58) Field of Classification Search .............. None
See application file for complete search history.

(56) References Cited

U.S. PATENT DOCUMENTS

| 4,957,735 | A | | 9/1990 | Huang |
| 5,013,556 | A | | 5/1991 | Woodle et al. |
| 5,213,804 | A | | 5/1993 | Martin et al. |
| 5,399,331 | A | | 3/1995 | Loughrey et al. |
| 7,135,177 | B2 | * | 11/2006 | Benz et al. ............... 424/143.1 |

FOREIGN PATENT DOCUMENTS

| EP | 0526700 A2 | 2/1993 |
| JP | 3502885 B | 7/1991 |
| JP | 4506518 B | 11/1992 |
| WO | WO 8302069 A | 6/1983 |
| WO | WO 8906692 A | 7/1989 |
| WO | WO 9422429 A | 10/1994 |
| WO | WO 9614864 A | 5/1996 |

OTHER PUBLICATIONS

Park et al (PNAS USA 1995;92:1327-1331).*
Blume et al (Biochimica Biophysica Acta 1993;1149:180-184).*
Fan et al (J Biol Chem. Nov. 4, 1994;269(44):27595-602.*
Sliwkowski et al (J. Biol. Chem 1994;269 (20):14661).*
Ahman et al. *Cancer Research*, 53:1484 (1993).
Allen et al. *Biochim. Biophys. Acta*, 1066: 29-36 (1991).
Allen et al. *Biochim. Biophys. Acta.*, 1068: 133-141 (1991).
Allen et al. *FEBS Lett.*, 223: 42-46 (1987).
Alving et al. *Immunol. Lett.*, 25: 275-280 (1990).
Blume et al. *Biochim, Biophys. Acta.*, 1029: 91-97 (1990).
Carter et al. *Proc. Natl. Acad. Sci. USA*, 89:4285 (1992).
Gabizon et al. *Eur. J. Cancer Clin. Oncol.*, 25: 1795-1803 (1989).
Hudziak et al. *Molecular and Cellular Biology*, 9:1165 (1989).
Klibanov et al. *Biochim. Biophys. Acta*, 1062:142-148 (1991).
Klibanov et al. *FEBS Lett.*, 268:235-237 (1990).
Lee et al. *Biochim. Biophys. Acta*, 1103:185-197 (1992).
Litzinger et al. *Biochemica et Biophysica Acta.*, 1127:249 (1992).
Lopez-Berestein et al. *J. Infect. Dis.*, 151: 704-710 (1985).
Mori et al. *FEBA 09850*, 284:263 (1991).
Papahadjopoulos et al., *Proc. Natl. Acad. Sci. USA*, 88:11460-11464 (1991).
Park et al. *R.B. Dickson and M.E. Lippman (eds), Genes Oncogenes, and Hormones: Advances in Cellular and Molecular Biology of Breast Cancer* Chapter 10 (1991).
Presant et al. *Cancer*, 62:905-911 (1988).
Sculier et al. *Eur. J. Cancer Clin. Oncol.*, 24:527-538 (1988).
Senior et al. *Biochim. Biophys. Acta.*, 1062:77-82 (1991).
Treat et al. *J. Natl. Cancer Inst.*, 82:1706-1710 (1990).
Woodle & Lasic. *Biochim. Biophys. Acta*, 1113:171-199 (1992).
Park et al., "Anti-p185HER2 monoclonal antibodies: Biological properties and potential for immunotherapy," *Genes, Oncogenes, and Hormones: Advances in Cellular and Molecular Biology of Breast Cancer,* R.B. Dickson and M.E. Lippman (eds.), pp. 193-211 (1991).
Hansen et al., "Attachment of antibodies to sterically stabilized liposomes: evaluation, comparison and optimization of coupling procedures," *Biochim Biophys Acta.* 1239:133-144 (1995).
Huang et al., "Microscopic Localization of Sterically Stabilized Liposomes in Colon Carcinoma-bearing Mics," *Cancer Research* 52:5135-5143 (Oct. 1, 1992).
Paul, William E., *Fundamental Immunology*, 4th Ed., Lippincott-Raven Publ., 45:1524-1525 (1998).
Hansen, Christian B., et al., "Attachment of antibodies to sterically stabilized liposomes: evaluation, comparison and optimization of coupling procedures," *Biochimica et Biophysica Acta* 1239 (1995) 133-144.
Allen T M et al, "Antibody-Mediated Targeting of Long-Circulating (Stealth R) Liposomes," Journal of Liposome Research, Mar. 1, 1994, pp. 1-25, vol. 4, No. 1.
Allen T M, "Long-Circulating (Sterically Stabilized) Liposomes for Targeted Drug Delivery," Trends in Pharmacological Sciences, Jan. 1, 1994, pp. 215-220, vol. 15.

* cited by examiner

*Primary Examiner*—Christopher H Yaen
(74) *Attorney, Agent, or Firm*—Townsend and Townsend and Crew LLP

(57) ABSTRACT

The present invention provides for immunoliposomes that optimizes internalization of a drug into target cells bearing a characteristic cell surface marker. The immunoliposomes comprise an Fab' domain of an antibody that specifically binds the characteristic marker, an amphipathic vesicle-forming lipid, and a polyethylene glycol derivatized lipid. The invention also provides for growth-inhibiting immunoliposomes that lack growth-inhibiting therapeutic agents and yet are capable of inhibiting the growth and proliferation of target cells.

10 Claims, 4 Drawing Sheets

IMMUNOLIPOSOMES THAT OPTIMIZE INTERNATIONALIZATION INTO TARGET CELLS

CROSS-REFERENCES TO RELATED APPLICATIONS

This is a continuation application of U.S. application Ser. No. 09/797,544, filed Feb. 28, 2001, now U.S. Pat. No. 7,135, 177, which is a continuation of U.S. application Ser. No. 08/634,197, filed Apr. 18, 1996, now U.S. Pat. No. 6,214,388, which is a continuation-in-part of U.S. application Ser. No. 08/336,860, filed Nov. 9, 1994, now abandoned; all three applications are hereby incorporated by reference for all purposes.

STATEMENT AS TO RIGHTS TO INVENTIONS MADE UNDER FEDERALLY SPONSORED RESEARCH OR DEVELOPMENT

This invention was made with Government support under Grant Nos. P50-CA58207, GM28117, CA36773 and CA25526, awarded by the National Institutes of Health. The Government of the United States has certain rights in this invention.

REFERENCE TO A "SEQUENCE LISTING," A TABLE, OR A COMPUTER PROGRAM LISTING APPENDIX SUBMITTED ON A COMPACT DISK.

Not applicable

FIELD OF THE INVENTION

The present invention relates to the field of liposomes. In particular, the present invention relates to liposomes specifically targeted to characteristic markers on target cells and which contain up to 4 mole percent of a hydrophilic polymer which results in an unexpected high rate of cellular incorporation.

BACKGROUND OF THE INVENTION

A number of pharmaceutical agents and potential pharmaceutical agents suffer from poor aqueous solubility, high levels of antigenicity, toxicity, or rapid degradation in serum which can hamper the development of suitable clinical formulations. One solution to these problems has been to encapsulate the pharmaceutical agent in a delivery vehicle that is soluble in aqueous solutions and that shields the agent from direct contact with tissues and blood. In particular, formulations based on liposome technology are of significant interest. Liposomes are vesicles comprised of concentrically ordered phospholipid bilayers which encapsulate an aqueous phase. They form spontaneously when phospholipids are exposed to aqueous solutions and can accommodate a variety of bioactive molecules.

Liposomes have proved a valuable tool as an in vivo delivery system for enhancing the efficacy of various pharmacologically active molecules (Ostro et al., *Liposomes from Biophysics to Therapeutics*, Dekker, New York, pp. 1-369 (1987)). Animal studies have shown that liposomes can decrease the toxicity of several antitumor and antifungal drugs, leading to clinical trials with promising results (Sculier et al., *Eur. J. Cancer Clin. Oncol.*, 24: 527-538; Gabizon, et al., *Eur. J. Cancer Clin. Oncol.*, 25: 1795-1803 (1989); Treat et al., *J. Natl. Cancer Inst.*, 82: 1706-1710 (1990); Lopez-Berestein et al., *J Infect. Dis.*, 151: 704-710 (1985); Presant et al., *Cancer,* 62: 905-911 (1988)). In addition, liposomes have been shown to be efficient carriers of antiparasitic drugs for treating intracellular infections of the reticuloendothelial system (RES), in activating macrophage cells to become tumoricidal, in models of metastasis, and in enhancing the immune response to encapsulated antigens, thus facilitating the formulation of artificial vaccines (Lopez-Berestein & Fidler, eds., *Liposomes in the Therapy of Infectious Diseases and Cancer*, Liss, New York (1989); Alving et al., *Immunol. Lett.,* 25: 275-280 (1990)).

All these effects stem from the capacity of macrophage cells in the liver and spleen (mononuclear phagocytic system MPS or reticuloendothelial system RES) to remove the majority of liposomes from the blood circulation within minutes (Gregoriadis, ed., *Liposomes as Drug Carriers*, Wiley, New York. (1988)). Such rapid clearance of liposomes however, has limited their prospects as an in vivo delivery system for transporting drugs to sites of disease beyond the RES.

Recent reports have described the use of various polymers to increase serum half-life of liposomes. In particular, it has been recognized that formulations of liposomes containing either mono-sialoganglioside ($GM_1$) or lipid derivatives of polyethylene glycol avoid MPS removal and significantly increase serum half-life (Allen et al., *FEBS Lett.*, 223: 42-46 (1987); Klibanov etal., *FEBS Lett.*, 268: 235-237 (1990); Blume etal., *Biochim, Biophys. Acta.*, 1029: 91-97 (1990); Allen et al., *Biochim. Biophys. Acta.*, 1066: 29-36 (1991); Papahadjopoulos et al., *Proc. Natl. Acad. Sci. USA,* 88: 11460-11464 (1991); Senior et al., *Biochim. Biophys. Acta.*, 1062: 77-82 (1991); Allen et al., *Biochim. Biophys. Acta.*, 1068: 133-141 (1991)).

Many reports have demonstrated that rapid removal of circulating liposomes in vivo by cells of the mononuclear phagocytic system (MPS) can be overcome by incorporation of lipids derivatized with the hydrophilic polymer polyethylene glycol (PEG). These liposomes are referred to as sterically stabilized or "stealth" liposomes. With PEG having a molecular weight in the range of 1000 to 5000, prolonged circulation and reduced MPS uptake is achieved (Woodle & Lasic., *Biochim. Biophys. Acta.*, 1113:171-199 (1992)). However, this reduction in clearance by the MPS is also associated with a reduction in uptake by a variety of cells (Lee, K. D. et al., *Biochim. Biophys. Acta.*, 1103:185-197 (1992)). In addition, the presence of hydrophilic polymers on the surface of the liposome appears to interfere with specific ligand recognition by targeting moieties conjugated to the liposome. Presumably this occurs due to steric hindrance of the active site of the targeting moiety by the long chain PEG molecules. (Klibanov et al., *Biochim. Biophys. Acta.* 1062: 148-148 (1991)).

Finally, while most therapeutic agents transported by liposomes must enter the cytoplasm of the target cell in order to express their biological activity, it is generally appreciated that most liposomes are either not actually internalized by the target cells, or, where uptake does occur, it is generally via an endocytotic pathway. Thus actual drug to the target cell typically entails release from the liposome (e.g., through disruption of the liposome itself or through "leakage") in the vicinity of the target cell and then subsequent uptake (either through diffusion, endocytosis, phagocytosis, or active transport) of the therapeutic agent from solution by the target cell. Indeed immunoliposomes have been designed to actually induce destabilization and fragmentation of the liposome once the targeting antibody has bound a target, thereby freeing the liposome contents (see, U.S. Pat. No. 4,957,735). Even these "target-sensitive" liposomes, lose a considerable amount of the therapeutic agent in solution before it can be taken up by the target cell. Alternatively, if the liposome is internalized by an endocytotic process, it is ultimately incorporated in a lysosome where strong acid conditions exist that can degrade a number of therapeutic agents (e.g. proteins).

Thus, delivery of effective doses of therapeutic agents to the cytoplasm of the target cell is hampered by low residence times in serum, ineffective targeting when residence times are increased, considerable loss of the therapeutic agent in solution before it may be taken up by the target cell, and degradation of the therapeutic in the endosomic/lysosomic pathway. Clearly, it would be desirable to obtain a liposome with increased serum half-life, capable of specifically targeting particular cells, and also capable of being internalized into the cytoplasm by the target cells thereby avoiding loss of the therapeutic agent or degradation by the endosomic/lysosomic pathway.

BRIEF SUMMARY OF THE INVENTION

The present invention provides novel immunoliposomes optimized for delivering therapeutic agents to the cytoplasm of a target cell. These immunoliposomes exhibit increased half-life in blood, are capable of specifically targeting particular cells, and are capable of being internalized into the cytoplasm by the target cells thereby avoiding loss of the therapeutic agents or degradation by the endolysosomal pathway.

Thus, in one preferred embodiment this invention provides for immunoliposomes that optimize internalization of a therapeutic agent into the cytoplasm of a cell bearing a characteristic cell surface marker. These immunoliposomes comprise an Fab' domain of an antibody wherein the Fab' domain specifically binds the characteristic marker, an amphipathic vesicle-forming lipid that forms a liposome, a polyethylene glycol derivatized lipid wherein the polyethylene glycol has an average molecular weight of between about 750 D and 5000 D, more preferably between about 1200 D and about 3000 D, most preferably about 1900 D, and a therapeutic agent contained within the liposome. The derivatized lipid is present at up to about 1.2 mole percent, more preferably at up to about 2.4 mole percent, and most preferably at up to about 3.6 mole percent of total lipid. Preferred characteristic markers include growth factor receptors. Particularly preferred are growth factor receptors including HER1, HER2, HER3 and HER4, with HER2 being most preferred. The Fab' domain may be a humanized Fab' domain, more specifically a humanized Fab' domain of an anti-HER2 monoclonal antibody. The growth-inhibiting immunoliposome may further comprise a maleimide-derivatized phosphatidylethanolamine (M-PE) which forms a thioether linkage to the Fab' domain of an antibody. The vesicle forming lipid may include a phospholipid, a glycolipid, a sphingolipid, or a sterol. The immunoliposomes have an average diameter that ranges from about 50 nm to about 500 nm, more preferably about 75 nm to about 300 nm and most preferably is about 100 nm. Therapeutic agents in the liposome may include daunomycin, idarubicin, mitoxantrone, mitomycin, cisplatin and other Platinum II analogs, vincristine, epirubicin, aclacinomycin, methotrexate, etoposide, doxorubicin, cytosine arabinoside, fluorouracil and other fluorinated pyrimidines, purines, or nucleosides, bleomycin, mitomycin, plicamycin, dactinomycin, cyclophosphamide and derivatives thereof, thiotepa, BCNU, taxol, taxotere and other taxane derivatives and isolates, camptothecins, polypeptides, a nucleic acid, a nucleic acid having a phosphorothioate internucleotide linkage, and a nucleic acid having a polyamide internucleotide linkage.

In one particularly preferred immunoliposome, the antibody Fab' domain is that of rhuMAbHER2, with the Fab' domain conjugated to maleimide-derivatized phosphatidylethanolamine (M-PE), the vesicle forming lipid is phosphatidylcholine (PC) and cholesterol (Chol) and the polyethylene glycol derivatized lipid is polyethylene glycol derivatized phosphatidylethanolamine (PEG-PE) where the polyethylene glycol component has a molecular weight of about 1900 D, and where the ratio PC:Chol:M-PE is 150:100:3 and the PEG-PE is present in an amount up to about 3.6 mole percent of total lipid.

In another particularly preferred embodiment, the antibody Fab' domain can be attached to the distal end of the polyethylene glycol derivatized lipid. In this case the immunoliposome can contain one polyethylene glycol derivatized lipid in which case, the Fab's domain is preferably attached to only a small fraction of the PEG-derivatized lipids, or alternatively, the immunoliposome can contain two or more different species of PEG-derivatized lipids in which case one species of PEG-derivatized lipid can serve as the linker for the Fab' antibody domain, while the other PEG-derivatized lipid, preferably present in higher concentration, provides "steric" stabilization thereby reducing liposome clearance rate. In one preferred embodiment, the Fab' attached to the PEG derivatized lipid comprises from about 0.6 mole percent to about 1 mole percent of total phospholipid, while total PEG-derivatized lipid comprises from about 10 mole percent to about 12 mole percent of total phospholipid. The Fab' is preferably attached to PEG-PE or to PEG-DSPE.

This invention also provides for a method of optimizing internalization of a therapeutic agent into a cell bearing a characteristic marker, the method comprising contacting the cell with any of the immunoliposomes summarized above and internalizing the liposome contents into the cytoplasm of the cell. This internalization may be by fusion of the liposome with cell membranes, or early exit from the endocytic vesicles.

In another preferred embodiment, this invention provides for a growth-inhibiting immunoliposome that specifically binds to a cell bearing a characteristic cell surface marker thereby inhibiting the proliferation or growth of that cell. The immunoliposome comprises an Fab' domain of an antibody where the Fab' domain specifically binds the marker and an amphipathic vesicle-forming lipid that forms a liposome. Unlike typical drug-delivery liposomes, however, this liposome contains no growth-inhibiting therapeutic agent and may contain no therapeutic agent at all. A composition may be identified as not being a growth-inhibiting therapeutic agent when the decrease in proliferation rate of target cells is less than 10 percent, more preferably less than 5 percent, more than the decrease in proliferation rate of the target cells caused by an "empty" liposome containing no agent (other than a neutral buffer or water) at all. Preferred characteristic markers include growth factor receptors. Particularly preferred are growth factor receptors including HER1, HER2, HER3 and HER4, with HER2 being most preferred. The Fab' domain may be a humanized Fab' domain, more specifically a humanized Fab' domain of an anti-HER2 (anti-p185HER2) monoclonal antibody. The growth-inhibiting immunoliposome may further comprise a maleimide derivatized phosphatidylethanolamine (M-PE) which forms a thioether linkage to the Fab' domain of an antibody. The vesicle forming lipid may include a phospholipid, a glycolipid, a sphingolipid, or a sterol. The growth-inhibiting immunoliposome may also comprise a hydrophilic polymer. Preferred hydrophilic polymers include polyethylene glycol, polypropylene glycol, mono-sialoganglioside ($GM_1$), phosphatidylinositol (PI) or cerebroside sulfate (CS)). Polyethylene glycol, when incorporated into the lipid will be incorporated as a polyethylene glycol derivatized lipid, preferably a polyethylene glycol derivatized phospholipid such as PEG-PE. The molecular weight of the polyethylene glycol may range from about 750 D to about 5000 D, more preferably from about 1200 D to about 3000 D, and most preferably is about 1900 D. The liposomes have an average diameter that ranges from about 50 nm to about 500 nm, more preferably about 75 nm to about 300 nm, and most preferably is about 100 nm. In one particularly preferred immunoliposome, the antibody Fab' domain is rhuMAbHER2, the Fab' domain is conjugated to M-PE, the vesicle forming lipid is phosphatidylcholine (PC) and cholesterol (Chol) and the polyethylene glycol derivatized lipid is polyethylene glycol derivatized phosphatidylethanolamine (PEG-PE) where the polyethylene glycol component has a molecular weight of about 1900 D, and where the ratio PC:Chol:M-PE is 150:100:3 and the PEG-PE is present in an amount up to about 3.6 mole percent of total lipid.

This invention also provides for a method of inhibiting growth of a cell bearing a characteristic marker, the method comprising contacting the cell with any of the growth-inhibiting liposomes summarized above.

In yet another embodiment, this invention also provides for pharmaceutical compositions comprising any of the growth-inhibiting or therapeutic-agent carrying immunoliposomes described above. The pharmaceutical compositions comprise a therapeutically effective dose of the immunoliposome and a pharmaceutically acceptable carrier or excipient.

DESCRIPTION OF THE PREFERRED EMBODIMENT

Definitions and General Parameters

Figure 1:
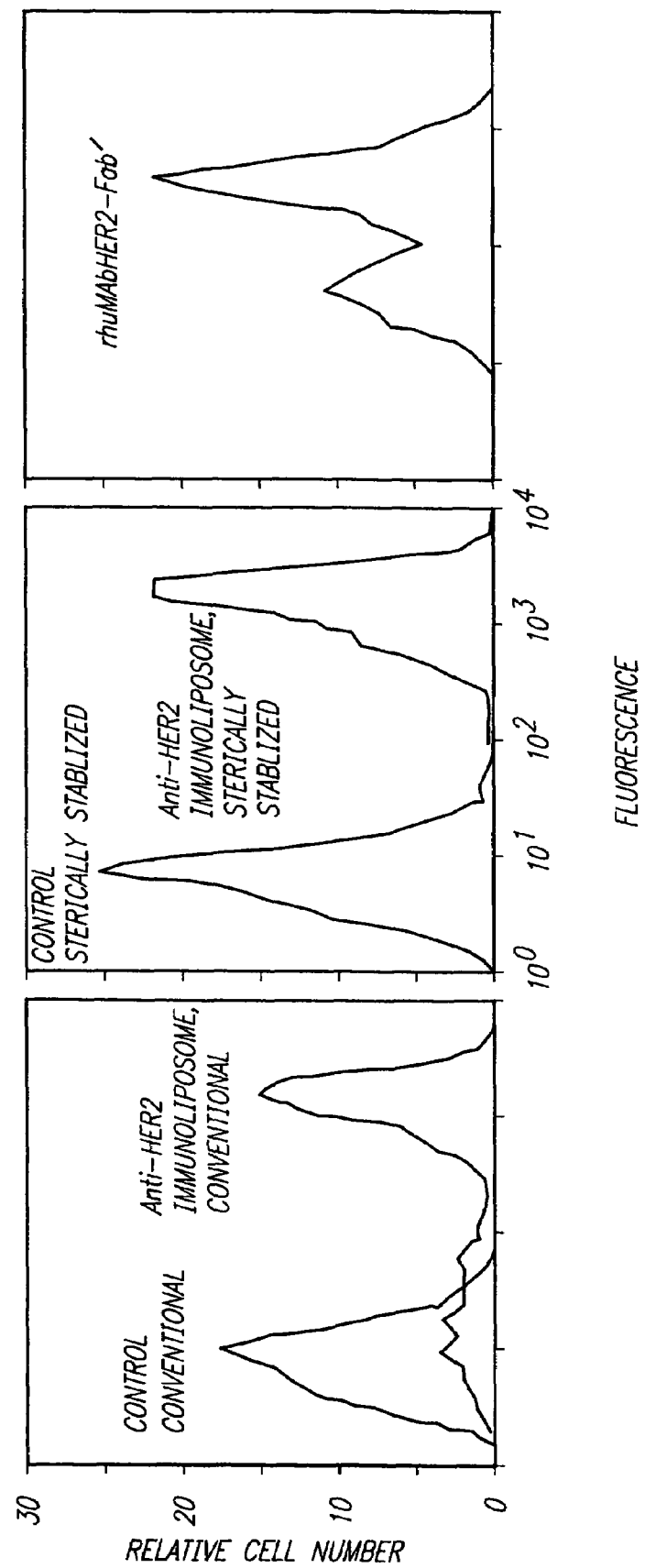
FIG. 1 illustrates flow cytometric histograms showing binding of anti-p185$^{HER2}$ immunoliposomes to SK-BR-3 cells. Immunoliposomes bound to SK-BR-3 cells after washing were detected by FITC-labeled goat anti-human IgG, which recognizes rhuMAbHER2 Fab' fragments. SK-BR-3 cells were incubated with conventional immunoliposomes (A), sterically stabilized (6 mole % PEG-PE) immunoliposomes (B), and free rhuMAbHER2-Fab' fragments (C) at equivalent antibody concentrations (3.3 µg/ml).

The following definitions are set forth to illustrate and define the meaning and scope of the various terms used to describe the invention herein.

The following abbreviations are used herein: DOX, doxorubicin; Chol, cholesterol; PA, phosphatidic acid; PC, phosphatidylcholine; PI, phosphatidylinositol; SM, sphinogmyelin; M-DPE, maleimide derivatized dipalmityolethanolarnine; PBS, phosphate buffered saline; LUV, large unilamellar vesicles; MLV, multilamellar vesicles; PE, phosphatidylethanolamine; PEG, polyethylene glycol; PEG-PE, polyethylene glycol derivatized phosphatidylethanolamine.

The term "amphipathic vesicle-forming lipid" is intended to include any. amphipathic lipid having hydrophobic and polar head group moieties, and which by itself can form spontaneously into bilayer vesicles in water, as exemplified by phospholipids, or (b) is stably incorporated into lipid bilayers in combination with phospholipids with its hydrophobic moiety in contact with the interior, hydrophobic region of the bilayer membrane, and its polar head group moiety oriented toward the exterior, polar surface of the membrane. An example of the latter type of vesicle-forming lipid is cholesterol and cholesterol derivatives such as cholesterol sulfate and cholesterol hemisuccinate.

As used herein, the term "specific binding" refers to that binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

The terms "ligand" or "targeting moiety", as used herein, refer generally to all molecules capable of specifically binding to a particular target molecule and forming a bound complex as described above. Thus the ligand and its corresponding target molecule form a specific binding pair. Examples include, but are not limited to antibodies, lymphokines, cytokines, receptor proteins such as CD4 and CD8, solubilized receptor proteins such as soluble CD4, hormones, growth factors, and the like which specifically bind desired target cells, and nucleic acids which bind corresponding nucleic acids through base pair complementarily. Particularly preferred targeting moieties include antibodies and-antibody fragments (e.g., the Fa' domain).

The term "immunoliposome" refers to a liposome bearing an antibody or antibody fragment that acts as a targeting moiety enabling the liposome to specifically bind to a particular "target" molecule that may exist in solution or may be bound to the surface of a cell. Where the target molecule is one that is typically found in relative excess (e.g., ≧10-fold) and in association with a particular cell type or alternatively in a multiplicity of cell types all expressing a particular physiological condition the target molecule is said to be a "characteristic marker" of that cell type or that physiological condition. Thus, for example, a cancer may be characterized by the overexpression of a particular marker such as the HER2 (c-erbB-2/neu) proto-oncogene in the case of breast cancer.

A "hydrophilic polymer" as used herein refers to long chain highly hydrated flexible neutral polymers attached to lipid molecules. Examples include, but are not limited to polyethylene glycol-, or polypropylene glycol-modified lipids PI or CS, or ganglioside $GM_1$.

The term "mole percent" when referring to the percentage of hydrophilic polymer in a liposome is expressed relative to the total lipid in the liposome unless otherwise stated. Thus, for example, in a liposome comprising a ratio of phosphatidylcholine (PC) to cholesterol (Chol) of 150:100, a 4 mole percent of hydrophilic polymer (e.g., PEG) would represent a ratio of PC:Chol:PEG of about 150:100:10.

The term "proliferation" refers to cell division or mitosis. Proliferation may be measured by standard assays such as by uptake of radioactive nucleotides (thymidine) or by direct observation.

Immunoliposomes In Drug Delivery

In one embodiment, the present invention provides immunoliposomes for selective delivery of therapeutic agents to specific tissues in a host and methods of use for those liposomes. The liposomes of this invention employ a composition that optimizes internalization of the liposome into the cytoplasm of the cells of the target tissue. The phrase "optimizes internalization" or "optimal internalization" is used to refer to the delivery of liposome contents such that it achieves maximum delivery to the cytoplasm of the target cell and therefore maximum therapeutic effect. It is recognized that internalization of an immunoliposome into the cytoplasm of a cell is a function of the blood half-life of the liposome, the ability of the liposome to recognize and bind to its target cell, and the uptake of the liposome into the cytoplasm of the target cell. It is well known that addition of a hydrophilic polymer to liposomes increases serum half-life by decreasing both liposome agglomeration (aggregation) and liposome uptake by the RES. Without being bound to a theory, it is believed that hydrophilic polymers at high concentrations interfere with recognition and binding by the targeting moiety or ligand and with subsequent uptake by the target cell, thereby decreasing the internalization of the liposome contents by the target cell. Optimal internalization into the cytoplasm of the cell refers to that condition in which maximal uptake into the cytoplasm of the target cell is achieved while still maintaining a blood half-life significantly greater than the blood half-life of liposomes lacking any hydrophilic polymer and adequate for targeting purposes.

In particular, this invention relies, in part, on the unexpected discovery that a liposome comprising a hydrophilic polymer (e.g., PEG-modified lipid) in an amount up to about 3.6 mole percent of total (vesicle-forming) lipid demonstrates an unexpected high rate of internalization into the cytoplasm of the target cell while retaining a blood half-life substantially greater than that seen in liposomes lacking a hydrophilic polymer. This is particularly true where the immunoliposome is targeted with Fab' fragments conjugated to one or more lipid constituents of the liposome.

In addition, it was also an unexpected discovery that when liposomes comprising up to 3.6 mole percent of a hydrophilic polymer were conjugated with an Fab' fragment of an antibody as a targeting moiety the liposome shows a high degree of cellular specificity and a binding affinity greater than that of the Fab' fragments alone. In fact, the binding specificity achieved by the immunoliposomes of the present invention is comparable to the binding specificity of the intact antibody. This result is particularly surprising since the intact antibody is a tetramer that comprises a pair of variable domain "arms" that are largely responsible for antibody specificity and avidity. Fab' regions, consisting of only one "arm" typically lack the specificity and binding avidity of the intact antibody. Thus they are typically expected to form poor targeting moieties.

While the Fab' fragment can be conjugated to any portion of the liposome, it was a surprising discovery of this invention that when the Fab' fragment is attached to the distal ends of the hydrophilic polymer (e.g., polyethylene glycol), high levels of internalization of the liposome by the target cell are achieved when even high levels of hydrophilic polymer are present (e.g., up to 15 mole percent of total phospholipid, more preferably from about 10 to 12 mole percent of total phospholipid). Thus, in one preferred embodiment, this invention provides for a liposome that is internalized by a target cell, where the liposome includes a Fab' fragment attached to the distal ends of the a hydrophilic polymer, e.g., polyethylene glycol. The Fab' fragment is preferably not attached to even the majority of hydrophilic polymer. Typically, the Fab' will be attached to only about 1 to about 20% of the hydrophylic polymer, more preferably about 4 to about 10 mole percent of the hydrophilic polymer and most preferably about 6 to about 10 mole percent of the hydrophilic polymer. The hydrophilic polymer bearing Fab' fragments (e.g., PEG-Fab') thus are present at about 0.1 to 2.0 mole percent of the total phospholipid, more preferably at about 0.4 to about 1.0 mole percent, and most preferably about 0.6 to about 1.0 mole percent of total phospholipid.

The immunoliposomes of this invention optimize delivery of therapeutic agents to the cytoplasm of the target cell by maintaining an elevated blood half-life, as compared to a liposome lacking a hydrophilic polymer, by maintaining a high degree of target specificity, and by effective internalization of the liposome itself (carrying therapeutic agent) thereby avoiding considerable loss of the therapeutic agent in solution or degradation of the therapeutic in the endosomic/lysosomic pathway. The liposomes of the present invention are thus particularly useful as vehicles for the delivery of therapeutics to specific target cells.

Immunoliposomes as Cell Growth Inhibitors

This invention also provides for growth-inhibiting immunoliposomes that may be utilized to inhibit tumor cell proliferation and thus provide an antitumor activity without encapsulating a growth-inhibiting therapeutic agent. In fact, the growth-inhibiting immunoliposomes of the present invention are effective when they contain no therapeutic agent. The growth-inhibiting immunoliposomes of this invention generally comprise an Fab' domain of an antibody that specifically binds to a cell bearing a characteristic marker, and an amphipathic vesicle forming lipid. In particular, the liposome may be conjugated to the Fab' domain of an anti-HER2 monoclonal antibody. In a preferred embodiment, the antibody is the Fab' fragment of the human monoclonal anti-HER2 antibody (rhuMAbHER2-Fab'). Unlike free rhuMAbHer2-Fab' in solution, liposomal (membrane) anchoring of the monovalent Fab' fragment results in antiproliferative and antitumor activity comparable to bivalent rhuMAbHER2. The antibody rhuMAbHER2-Fab' in solution does not have this property. Without being bound to a particular theory, it is believed that membrane anchoring of the Fab' fragment in the anti-HER2 immunoliposome confers this antiproliferative property presumably by enabling cross-linking of p185$^{HER2}$ on the tumor cell surface.

The Fab' fragments can be conjugated to any portion of the liposome. Thus, for example, in one embodiment, the Fab' can be conjugated directly to the liposome, while in another embodiment, the Fab's can be conjugated to the hydrophilic polymer (e.g., PEG).

As indicated above, the growth-inhibiting immunoliposomes do not contain a growth-inhibiting agent. A "growth-inhibiting agent" refers to a chemical agent that reduces the growth rate of cells to which it is administered. In the extreme case a growth-inhibiting agent may be cytotoxic to the cell to which it is administered. As used herein the growth rate of cells refers to the rate of proliferation of the cells. Increased proliferation rate is typically associated with increased metabolic rate and thus proliferation rates may be assayed by detecting metabolic rates (e.g., by uptake of a labeled metabolic precursor such as tritiated thymidine). Thus, increased growth or proliferation rate may be taken as indicating an increased metabolic rate or vice versa.

Growth-inhibiting agents are well known to those of skill in the art and include, but are not limited to doxorubicin, ricin A, gelonin. It will be recognized that some compositions (e.g., antibiotics) may exhibit minor growth inhibitory activity as an incidental consequence of their primary activity. Such compositions are not considered herein to be growth-inhibiting agents. The phrase a "liposome containing no growth-inhibiting therapeutic agent" is intended to capture the fact that the inhibition of cell growth and proliferation obtained with the growth-inhibiting immunoliposomes of the present invention is a consequence of the liposome/Fab' construct itself and is not a consequence of the liposome contents. Thus, a growth inhibiting agent, as used herein refers to an agent that, when present in the growth inhibiting immunoliposome, results in a decrease in cell proliferation rate at least 10 percent greater than the decrease in cell proliferation rate observed by administration of the same immunoliposomes lacking any therapeutic or growth inhibiting agent.

While the growth-inhibiting liposomes of this invention will inhibit cell growth and proliferation even when they carry no therapeutic agent and therefore may be administered "empty", one of skill will appreciate that it may be desirable to encapsulate a therapeutic agent other than a growth-inhibiting therapeutic agent thereby achieving a liposome that shows dual, additive or supradditive activities. Thus, for example, an immunoliposome loaded with an antibiotic will show both antibiotic activity as well as the ability to inhibit growth and proliferation of the target cells.

The growth-inhibiting liposomes and the therapeutic agent-carrying immunoliposomes of the present invention may be utilized to inhibit tumor cell proliferation or to target therapeutics to specific cells in a wide variety of hosts. Preferred hosts include mammalian species such as humans, non-human primates, dogs, cats, cattle horses, sheep, rodents, largomorphs and the like.

Liposome Composition

In general, the immunoliposomes of the present invention comprise one or more vesicle-forming lipids, an Fab' domain of an antibody which acts as a targeting moiety and, especially in the case of the therapeutic agent delivering immunoliposomes, a hydrophilic polymer. Without being bound to a particular theory the vesicle-forming lipids act to form a bilayer which encapsulates the therapeutic agent when it is present, the hydrophilic polymer serves to prevent agglomeration of the liposomes and also to decrease uptake of the liposome by the RES and thereby increase blood half-life, and the ligand serves to specifically bind the liposomes to a cell or tissue bearing a target (i.e., a characteristic marker) for which the ligand is specific. The low mole percentage of the hydrophilic polymer coupled with the use of the Fab' antibody fragment allows specific targeting of the liposome and unexpectedly results in a high level of internalization of the entire liposome into the cytoplasm of the target cell.

A) Vesicle-Forming Lipids

The vesicle-forming lipid is preferably one having two hydrocarbon chains, typically acyl chains and a polar head group. Included in this class are the phospholipids, such as phosphaddylcholine (PC), phosphatidylethanolamine (PE), phosphatidic acid (PA), phosphatidylinositol (PI) and sphingomyelin (SM), where the two hydrocarbon chains are typically between about 14-22 carbon atoms in length and have varying degrees of unsaturation or 14-18 carbon chain saturated phospholipids. Also included in this class are the glycolipids such as cerebrosides and gangliosides.

In a preferred embodiment, the major lipid component in the liposomes is phosphatidylcholine. Phosphatidylcholines having a variety of aryl chain groups of varying chain length and degree of saturation are available or may be isolated or synthesized by well-known techniques. In general, less saturated phosphatidylcholines are more easily sized, particularly when the liposomes must be sized below about 0.3 microns, for purposes of filter sterilization. Phosphatidylcholines containing saturated fatty acids with carbon chain lengths in the range of $C_{14}$ to $C_{22}$ are preferred. Phosphatidylcholines with mono or diunsaturated fatty acids and mixtures of saturated and unsaturated fatty acids may also be used. Liposomes useful in the present invention may also be composed of sphingomyelin or phospholipids with head groups other than choline, such as ethanolamine, serine, glycerol and inositol. In particular, phospholipids suitable for formation of liposomes useful in the methods and compositions of the present invention include, e.g., phosphatidylcholine, phosphatidylglycerol, lecithin, β, γ-ydipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myristoyl-phosphatidylserine, di-oleyl-phosphatidylcholine, and the like. Non-phosphorus containing lipids may also be used in the liposomes of the compositions of the present invention. These include, e.g., stearylamine, docecylamine, acetyl palmitate, fatty acid amides, and the like. Additional lipids suitable for use in the liposomes of the present invention are well known to persons of skill in the art and are cited in a variety of well known sources, e.g., *McCutcheon's Detergents and Emulsifiers and McCutcheon's Functional Materials*, Allured Publishing Co., Ridgewood, N.J., both of which are incorporated herein by reference. Preferred liposomes will include a sterol, preferably cholesterol, at molar ratios of from 0.1 to 1.0 (cholesterol:phospholipid). Most preferred liposome compositions are phosphatidylcholine/cholesterol, distearoylphosphatidylcholine/cholesterol, dipalmitoylphosphatidylcholine/cholesterol, and sphingomyelin/cholesterol. Small amounts (ie., <10%) of other derivatized lipids are often present in liposomes having these compositions.

According to one important feature of the invention, the vesicle-forming lipid may be a relatively fluid lipid, typically meaning that the lipid phase has a relatively low liquid to liquid-crystalline melting temperature, e.g., at or below room temperature, or a relatively rigid lipid, meaning that the lipid has a relatively high melting temperature, e.g., up to 60° C. As a rule, the more rigid, i.e., saturated lipids, contribute to membrane rigidity in a lipid bilayer structure and also contribute to greater bilayer stability in blood. Other lipid components, such as cholesterol, are also known to contribute to membrane rigidity and stability in lipid bilayer structures. As mentioned above, a long chain (e.g. $C_{14}$-$C_{22}$) saturated lipid plus cholesterol is one preferred composition for delivering therapeutic compositions to target tissues, such as solid tumors, since these liposomes do not tend to release the drugs into the plasma as they circulate through the blood stream. Phospholipids whose acyl chains have a variety of degrees of saturation can be obtained commercially. For example, egg phosphatidylcholine (EPC) can be purchased from Avanti Polar Lipids (Alabaster, Ala.) and hydrogenated soy phosphatidylcholine (HSPC) can be obtained from Natterman (Cologne, FRG). Alternatively, phospholipids can be prepared according to published methods. (see D. M. Small, "The physical chemistry of lipids" (1986) Plenum Press, N.Y., or D. D. Lasic, "Liposomes: from physics to applications" (1993) Elsevier, Amsterdam; N.Y.)

B) Hydrophilic Polymer.

As noted above the presence of hydrophilic polymers tends to increase the blood half-life of a liposome. (See, for example, Woodle, et al. *Biochim. Biophys. Acta.,* 1113: 171-199 (1992).) Thus, it is often desirable to add a hydrophilic polymer such as polyethylene glycol (PEG)-modified lipids or ganglioside $G_{m1}$ to the liposomes. Addition of such components prevents liposome aggregation during coupling of the targeting moiety to the liposome. These components also provides a means for increasing circulation lifetime of the phospholipid. However, it has been observed that while hydrophilic polymers decrease liposome uptake by the RES and thereby increase blood half-life, there is a corresponding decrease in uptake by target tissues as well. It was an unexpected discovery of the present invention that a concentration of hydrophilic polymer (e.g., PEG) of 1 to 4 mole percent of vesicle-forming lipid (excluding cholesterol) provides optimal cellular uptake combined with adequate blood half-life.

A number of different methods may be used for the preparation of PEG for incorporation into liposomes. In a preferred embodiment, PEG is incorporated as PEG derivatized phosphatidylethanolamine (PEG-PE) or PEG derivatized distearoyl phosphatidylethanolamine (PEG-DSPE). Methods of preparing PEG-PE are well known and typically involve using an activated methoxy PEG (with only one reactive end) and PE. Thus PEG-succinimidyl succinate may be reacted in a basic organic solvent (Klibanov et al., *FEBS Lett.,* 268: 235-237 (1990)). A particularly preferred method of PEG-PE preparation is based on reaction of the PEG with carbonyldiimidazole followed by addition of PE (see, Woodle et al. *Proc. Intern. Symp. ControL Rel. Bioact. Mater.,* 17: 77-78 (1990), Papahadjopoulos et al., *Proc. Natl. Acad. Sci. USA,* 88: 11460-11464 (1991), Allen et al., Biochim. Biophys. Acta., 1066: 29-36 (1991), Woodle et al., *Biochim. Biophys. Acta.m,* 1105: 193-200 (1992), and Woodle et al, *Period. Biol.,* 93: 349-352 (1991)). Similarly, cyanuric chloride activated PEG in a basic organic solvent is described by Blume et al. *Biochim. Biophys. Acta.,* 1029: 91-97 (1990) and U.S. Pat. No. 5,213,804 which is herein incorporated by reference. A completely different approach is based on coupling the PEG with preformed liposomes utilizing tresyl chloride activated PEG which is then added to liposomes containing PE at high pH (Senior et al., *Biochim. Biophys. Acta.,* 1-62: 77-82 91991). Derivatized PEG is also commercially available. Thus, for example, PEG-PE is available from Avanti Polar lipids (Alabaster, Ala.) or Liposome Technology (Menlo Park, Calif., USA). One of skill in the art will recognize that many other linkages are available.

C) Fab' Antibody Fragment

In a preferred embodiment, the liposomes of the present invention are conjugated to the Fab' region of an antibody which acts as a targeting moiety enabling the liposome to specifically bind a target cell bearing the target molecule (e.g., characteristic marker) to which the Fab' antibody fragment is directed. In general terms, the Fab' region of an antibody represents a monomer comprising the variable regions and the $C_H1$ region of one arm of an antibody.

An "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies may exist as intact immunoglobulins or as a number of well characterized fragments produced by digestion with various peptidases. In particular, pepsin digests an antibody below the disulfide linkages in the hinge region to produce F(ab)'$_2$, a dimer of Fab which itself is a light chain joined to $V_H$-$C_H1$ by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially an Fab with part of the hinge region (see, *Fundamental Immunology*, W. E. Paul, ed., Raven Press, N.Y. (1993) for more antibody fragment terminology). While the Fab' domain is defined in terms of the digestion of an intact antibody, one of skill will appreciate that such Fab' fragments may be synthesized de novo either chemically or by utilizing recombinant DNA methodology.

The Fab' regions used in the present invention may be derived from antibodies of animal (especially mouse or rat) or human origin or may be chimeric (Morrison et al., *Proc Natl. Acad. Sci. USA* 81, 6851-6855 (1984) both incorporated by reference herein) or humanized (Jones et al., *Nature* 321, 522-525 (1986), and published UK patent application No. 8707252, both incorporated by reference herein).

The Fab' region is selected to specifically bind to a molecule or marker characteristic of the surface of the cells to which it is desired to deliver the contents of the liposome. A molecule is characteristic of cell, tissue, or physiological state when that molecule is typically found in association with that cell type or alternatively in a multiplicity of cell types all expressing a particular physiological condition (e.g., transformation). A specific characteristic marker is preferably found on the surfaces of cells of a particular tissue or cell type or on the surfaces of tissues or cells expressing a particular physiological condition and on no other tissue or cell type in the organism. One of skill will recognize however, that such a level of specificity of the marker is often not required. For example a characteristic cell surface marker will show sufficient tissue specificity if the only non-target tissues are not accessible to the liposome. Alternatively, effective specificity may be achieved by overexpression of the marker in the target tissue as compared to other tissues. This will result in preferential uptake by the target tissue leading to effective tissue specificity. Thus for example, many cancers are characterized by the overexpression of cell surface markers such as the HER2 (c-erbB-2, neu) proto-oncogene encoded receptor in the case of breast cancer.

One of skill will recognize that there are numerous cell surface markers that provide good characteristic markers for liposomes depending on the particular tissue it is desired to target. These cell surface markers include, but are not limited to carbohydrates, proteins, glycoproteins, MHC complexes, and receptor proteins such as HER, CD4 and CD8 receptor proteins as well as other growth factor receptor proteins.

Growth factor receptors are particularly preferred characteristic cell surface markers. Growth factor receptors are cell surface receptors that specifically bind growth factors and thereby mediate a cellular response characteristic of the particular growth factor. The term "growth factor", as used herein, refers to a protein or polypeptide ligand that activates or stimulates cell division or differentiation or stimulates biological response like motility or secretion of proteins. Growth factors are well known to those of skill in the art and include, but are not limited to, platelet-derived growth factor (PDGF), epidermal growth factor (EGF), insulin-like growth factor (IGF), transforming growth factor β (TGF-β), fibroblast growth factors (FGF), interleukin 2 (IL2), nerve growth factor (NGF), interleukin 3 (IL3), interleukin 4 (IL4), interleukin 1 (IL1), interleukin 6 (IL6), interleukin 7 (IL7), granulocyte/macrophage colony-stimulating factor (GM-CSF), granulocyte colony-stimulating factor (G-CSF), macrophage colony-stimulating factor (M-CSF), erythropoietin and the like. One of skill in the art recognizes that the term growth factor as used herein generally includes cytokines and colony stimulating factors.

Particularly preferred markers are found in the HER family of growth factor receptors. More specifically HER1, HER2, HER3 and HER4 are more preferred with HER2 most preferred. The HER receptors comprise protein tyrosine kinases that themselves provide highly specific antibody targets. Thus, in one embodiment, the P185 tyrosine kinase of HER2 provides a most preferred target for the Fab' antibody domain of the utilized in the immunoliposomes of the present invention.

It will be appreciated that the characteristic marker need not be a naturally occurring marker, but rather may be introduced to the particular target cell. This may be accomplished by directly tagging a cell or tissue with a particular marker (e.g., by directly injecting the particular target tissue with a marker, or alternatively, by administering to the entire organism a marker that is selectively incorporated by the target tissue. In one embodiment, the marker may be a gene product that is encoded by a nucleic acid in an expression cassette.

The marker gene may be under the control of a promoter that is active only in the particular target cells. Thus introduction of a vector containing the expression cassette will result in expression of the marker in only the particular target cells. One of skill in the art will recognize that there are numerous approaches utilizing recombinant DNA methodology to introduce characteristic markers into target cells.

In one preferred embodiment, the targeting moiety will specifically bind products or components of a growth factor receptor, to particular products of the HER2 (c-erbB-2, neu) proto-oncogene. It is particularly preferred that the targeting moiety bind the growth factor receptor-tyrosine kinase encoded by HER2, protein p185$^{HER2}$, which is commonly overexpressed in breast cancers (Slamon et al., Science, 235: 177-182 (1987). Other suitable targets for the targeting moiety include, but are not limited to EGFR (HER1), HER3, and HER4, combinations of these receptors, and other markers associated with cancers. Other antibodies of interest include, but are not limited to BR96 (Friedman et al., *Cancer Res.*, 53: 334-339 (1993), e23 to erbB2 (Batra et al, *Proc. Natl. Acad. Sci. USA,* 89: 5867-5871 (1992)), PR1 in prostate cancer (Brinkmann et al., *Proc. Natl. Acad. Sci. USA.*, 90: 547-551 (1993)), and K1 in ovarian cancer (Chang et al. *Int. J. Cancer,* 50: 373-381 (1992).

Immunoliposomes of the present invention may be prepared by incorporating the Fab' antibody domain moieties into the liposomes by a variety of techniques well known to those of skill in the art. For example, a biotin conjugated Fab' may be bound to a liposome containing a streptavidin. Alternatively, the biotinylated Fab' may be conjugated to a biotin derivatized liposome by an avidin or streptavidin linker. Thus, for example, a biotinylated monoclonal antibody was biotinylated and attached to liposomes containing biotinylated phosphatidylethanolamine by means of an avidin linker. (See, for example, Ahmad et al., *Cancer Res.,* 52: 4817-4820 (1992) which is herein incorporated by reference). Typically about 30 to 125 and more typically about 50 to 100 Fab' molecules per liposome are used.

In a preferred embodiment, the targeting moiety may be directly conjugated to the liposome. Such means of direct conjugation are well known to those of skill in the art. See for example, G. Gregoriadis, (1984) "Liposome Technology" CRC Press, Boca Raton, Fla. and D. D. Lasic, "Liposomes: from physics to applications" (1993) Elsevier, Amsterdam; N.Y. Particularly preferred is conjugation through a thioether linkage. This may be accomplished by reacting the antibody with a maleimide derivatized lipid such as maleimide derivatized phosphatidylethanolamine (M-PE) or dipalmitoylethanolamine (M-DEP). This approach is described in detail by Martin et al. *J. Biol. Chem.*, 257: 286-288 (1982) which is incorporated herein by reference.

In another preferred embodiment, the targeting moiety. (e.g., the Fab' fragment) can be attached to the hydrophilic polymer (e.g., a PEG). Means of attaching targeting molecules to polymer linkers are well known to those of skill in the art (see, e.g., chapter 4 in *Monoclonal Antibodies: Principles and Applications*, Birch and Lennox, eds., John Wiley & Sons, Inc., New York (1995); and Blume et al. *Biochem. Biophys. Acta.* 1149: 180-184 (1993). In a particularly preferred embodiment, an Fab' fragment is linked to a maleimide derivatized PEG through the -SII group of th Fab'. To provide a linker group, α-distearoylphosphatidylethanolaminocarbonyl-ω-malimidopropionylamidopolyethylene glycol is synthesized from distearoylphosphatidylethanolamine and heterobifinctional PEG derivative, N-hydroxysuccinimidyl-PEG-maleimide according to standard methods. The maleimide-derivitive of PEG-PE is included in the liposome preparation as described above and below and the Fab' fragment can be conjugated with the liposome via the sulfhydryl group at pH 7.2.

Preparation of Liposomes

A variety of methods are available for preparing liposomes as described in; e.g., Szoka et al., *Ann. Rev. Biophys. Bioeng.* 9:467 (1980), U.S. Pat. Nos. 4,186,183, 4,217,344, 4,235, 871, 4,261,975, 4,485,054, 4,501,728, 4,774,085, 4,837,028, 4,946,787, PCT Publication No. WO 91/17424, Szoka & Papahadjopoulos, *Proc. Natl. Acad. Sci. USA,* 75: 4194-4198 (1978), Deamer and Bangham, *Biochim. Biophys. Acta,* 443: 629-634 (1976); Fraley, et al., *Proc. Natl. Acad. Sci. USA,* 76: 3348-3352 (1979); Hope, et al., *Biochim. Biophys. Acta,* 812: 55-65 (1985); Mayer, et al., *Biochim. Biophys. Acta,* 858: 161-168 (1986); Williams, et al., *Proc. Natl. Acad. Sci.,* 85: 242-246 (1988), the text *Liposomes,* Marc J. Ostro, ed., Marcel Dekker, Inc., New York, 1983, Chapter 1, and Hope, et al., *Chem. Phys. Lip.* 40: 89 (1986), all of which are incorporated herein by reference. Suitable methods include, e.g., sonication, extrusion, high pressure/homogenization, microfluidization, detergent dialysis, calcium-induced fusion of small liposome vesicles, and ether-infusion methods, all well known in the art. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents such as deoxycholate.

In a preferred embodiment, multilamellar liposomes are produced by the reverse phase evaporation method of Szoka & Papahadjopoulos, *Proc. Natl. Acad. Sci. USA,* 75: 4194-4198 (1978).

Unilamellar vesicles are generally prepared by sonication or extrusion. Sonication is generally performed with a tip sonifier, such as a Branson tip sonifier, in an ice bath. Typically, the suspension is subjected to several sonication cycles. Extrusion may be carried out by biomembrane extruders, such as the Lipex Biomembrane Extruder. Defined pore size in the extrusion filters may generate unilamellar liposomal vesicles of specific sizes. The liposomes may also be formed by extrusion through an asymmetric ceramic filter, such as a Ceraflow Microfilter, commercially available from the Norton Company, Worcester Mass.

Following liposome preparation, the liposomes which have not been sized during formation may be sized to achieve a desired size range and relatively narrow distribution of liposome sizes. A size range of about 0.2-0.4 microns allows the liposome suspension to be sterilized by filtration through a conventional filter, typically a 0.22 micron filter. The filter sterilization method can be carried out on a high through-put basis if the liposomes have been sized down to about 0.2-0.4 microns.

Several techniques are available for sizing liposomes to a desired size. One sizing method is described in U.S. Pat. Nos. 4,529,561 or 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, *Ann. Rev. Biophys. Bioeng.,* 10: 421-450 (1981), incorporated herein by reference. Average liposome diameter may be reduced by sonication of formed liposomes. Intermittent sonication cycles may be alternated with QELS assessment to guide efficient liposome synthesis.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. For use in the present invention, liposomes having a size of about 0.05 microns to about 0.15 microns. More preferred are liposomes having a size of about 0.05 to 0.5 microns.

Immunoliposome Contents

The therapeutic agent which may be used is any compound including the ones listed below which can be stably entrapped in liposomes at a suitable loading factor and administered at a therapeutically effective doses (indicated below in parentheses after each compound, $m^2$ refers to body surface area). These include amphipathic antitumor compounds such as the plant alkaloids vincristine (1.4 $mg/m^2$), vinblastine (4-18 $mg/m^2$) and etoposide (35-100 $mg/m^2$ ), and the anthracycline antibiotics including doxorubicin (60-75 $mg/m^2$), epirubicin (60-120 $mg/m^2$ ) and daunorubicin (25-45 $mg/m^2$). The water-soluble anti-metabolites such as methotrexate (3 $mg/m^2$), cytosine arabinoside (100 $mg/m^2$) and fluorouracil (10-15 mg/kg), the antibiotics such as bleomycin (10-20 units/$m^2$, mitomycin (20 $mg/m^2$), plicamycin (25-30 $\mu g/m^2$) and dactinomycin (15 $\mu g/m^2$), and the alkylating agents including cyclophosphamides and derivatives thereof (3-25 mg/kg), thiotepa (0.3-0.4 mg/kg) and BCNU (150-200) $mg/m^2$) are also useful in this context. Other suitable drugs include aclacinomycin, idarubicin, mitoxantrone, cisplatin and other Platinum II analogs. The liposomes may also contain the taxanes including taxol, taxotere, dihydroxytaxanes, camptothecines and other taxane derivatives and isolates. In addition, the liposomes may contain encapsulated tumor-therapeutic peptides (e.g., plant or bacterially derived toxins) and protein drugs such as IL-2 and/or TNF, and/or immunomodulators, such as M-CSF, which are present alone or in combination with anti-tumor drugs, such as anthracycline antibiotic drugs. The immunoliposomes may contain fluorinated pyramidine and purine bases or nucleosides. The immunoliposomes may also contain nucleic acids such as oligonucleotides containing natural or modified bases and having a phosphodiester internucleotide linkage or modified internucleotide linkages such as a phosphorothioate or polyamide linkages. One of skill will recognize that nucleic acids may be used as antisense or triplex-forming molecules to block transcription and translation through binding of DNA or RNA. Alternatively, the nucleic acids may be used to transform cells and to induce the expression of heterologous proteins. In this latter context, the nucleic acid will comprise an expression cassette which includes the nucleic acid sequence encoding the protein to be expressed under the control of a promoter.

Loading Therapeutic Compositions into Immunoliposomes

The methods of loading conventional drugs into liposomes are well known to those of skill in the art. The most common methods include an encapsulation technique and the transmembrane potential loading method. In the encapsulation technique, the drug is placed into the buffer from which the liposomes are made. The latter method has been described in detail in U.S. Pat. No. 4,885,172, U.S. Pat. No. 5,059,421, and U.S. Pat. No. 5,171,578, the contents of which are incorporated herein by reference.

Briefly, the transmembrane potential loading method can be used with essentially any conventional drug which can exist in a charged state when dissolved in an appropriate aqueous medium. Preferably, the drug will be relatively lipophilic so that it will partition into the liposome membranes. A transmembrane potential is created across the bilayers of the liposomes or targeting moiety liposome conjugates and the drug is loaded into the liposome by means of the transmembrane potential. The transmembrane potential is generated by creating a concentration gradient for one or more charged species (e.g., $Na^+$, $K^+$ and/or $H^+$) across the membranes. This concentration gradient is generated by producing liposomes or targeting moiety liposome conjugates having different internal and external media. Thus, for a drug which is positively charged when ionized, a transmembrane potential is created across the membranes which has an inside potential which is negative relative to the outside potential, while for a drug which is negatively charged, the opposite orientation is used.

Assaying Blood Half-life

One of the requirements for liposome localization in a target tissue is an extended immunoliposome lifetime in the bloodstream following administration. One measure of immunoliposome lifetime in the bloodstream is the blood/RES ratio determined at a selected time after liposome administration. Typically immunoliposomes containing a label (e.g. fluorescent marker, electron dense reagent, or radioactive marker), either internal in the liposome or bound to a lipid comprising the liposome, are injected into the test organism. A fixed period of time later, the organism is sacrificed and the amount of label detected in the blood (e.g. by measuring luminescence, or scintillation counting) is compared to that localized in particular tissues (e.g. liver or spleen).

The time course of retention of immunoliposomes in the blood may also simply be determined by sampling blood at fixed intervals after administration of label-containing liposomes and determining the amount of label remaining in the circulation. The result may be expressed as the fraction of the original dose.

Assaying Uptake Into the Cytoplasm of Target Cells and Determining Tissue Distribution Uptake and internalization of immunoliposomes into the cytoplasm of target cells may similarly be determined by administering immunoliposomes containing a label (e.g. fluorescent marker, electron dense reagent, or radioactive marker) and subsequently detecting the presence or absence of that label in the cytoplasm of the target cell. For example an immunoliposome containing a fluorescent marker, such as rhodamine conjugated to the lipid constituting the liposome itself, may be administered to the organism or simply to cells in culture. The tissues or cells may then be fixed and the fluorescence detected using fluorescence microscopy. Similarly, an electron-dense label (e.g. gold) may be used and detected using electron microscopy. One of skill in the art will recognize that many labels are suitable and the method of detection will reflect the choice of label.

Assaying for Antiproliferative Activity of Immunoliposomes

The present invention provides for growth-inhibiting immunoliposomes that essentially comprise an empty immunoliposome having an Fab' targeting moiety directed to a cell surface receptor. Particularly preferred are growth factor receptors. Identification of Fab' immunoliposomes that are particularly effective inhibitors of cell proliferation may be accomplished with routine screening. This involves providing a cell culture where the cells bear a growth factor receptor, or other characteristic cell surface marker, to which the Fab' fragment is directed, contacting the cells in the culture with the immunoliposome to be tested, and measuring the resulting change in cell proliferation rate. Means of measuring cell proliferation rate are well known to those of skill in the art.

In one approach, for example, proliferation rate may be assessed directly by measuring the change in actual numbers of cells over a fixed period of time. Thus, as illustrated in Example 3, tumor cells such as SK-BR-3 or BT-474 cells were grown in monolayer culture and then incubated at 37° C. with varying concentrations of immunoliposomes based on antibody content. After continuous treatment for 4 days, cell monolayers were washed with PBS and stained with crystal violet dye (0.5% in methanol) for determination of relative proliferation as previously described (Hudziak, et al., *Mol. Cell Biol.* 9: 1165-1172 (1989) which is incorporated herein by reference).

Alternatively, it is well known that increases in cell proliferation rate are typically accompanied by increases in metabolic rate. Thus proliferation may be evaluated indirectly by measuring changes in metabolic rate of cells exposed to the immunoliposome to be tested. Numerous means of measuring metabolic rate are well known to those of skill in the art. On particularly preferred approach is to measure the rate of uptake of a labeled metabolic precursor such as tritiated thymidine. Briefly this is accomplished by administering the [$^3$H]-thymidine to a test culture containing the immunoliposome and to a control culture lacking the immunoliposome. After a fixed period of time, cells are collected and the amount of [$^3$H]-thymidine taken up by the cells is measured utilizing standard techniques (e.g., scintillation counting). Comparison of the test and control cells indicates changes in metabolic activity and therefore proliferation rate.

Pharmaceutical Compositions

Pharmaceutical compositions comprising the immunoliposomes of the invention are prepared according to standard techniques and further comprise a pharmaceutically acceptable carrier. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the liposome suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The concentration of immunoliposomes, in the pharmaceutical formulations can vary widely, i. e., from less than about 0.05%, usually at or at least about 2-5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, immunoliposomes composed of irritating lipids may be diluted to low concentrations to lessen inflammation at the site of administration. The amount of immunoliposome administered will depend upon the particular Fab' used, the disease state being treated, the therapeutic agent being delivered, and the judgement of the clinician. Generally the amount of immunoliposomes administered will be sufficient to deliver a therapeutically effective dose of the particular pharmacological agent. The quantity of immunoliposomes necessary to deliver a therapeutically effective dose can be determined by uptake assays as described above. Therapeutically effective dosages for various pharmacological agents are well known to those of skill in the art and representative ranges are given for a number of pharmaceuticals above. Typical immunoliposome dosages will generally be between about 0.01 and about 50 mg per kilogram of body weight, preferably between about 0.1 and about 10 mg/kg of body weight.

Preferably, the pharmaceutical compositions are administered parenterally, i.e., intraarticularly, intravenously, intraperitoneally, subcutaneously, or intramuscularly. More preferably, the pharmaceutical compositions are administered intravenously or intraperitoneally by a bolus injection. Particular formulations which are suitable for this use are found in *Remington's Pharmaceutical Sciences*, Mack Publishing Company, Philadelphia, Pa., 17th ed. (1985). Typically, the formulations will comprise a solution of the liposomes suspended in an acceptable carrier, preferably an aqueous carrier. A variety of aqueous carriers may be used, e.g., water, buffered water, 0.9% isotonic saline, and the like. These compositions may be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

EXAMPLES

The invention is illustrated by the following examples. These examples are offered to illustrate, but not to limit the present invention.

Example 1

Preparation of Liposomes and Immunoliposomes

A) Materials

Egg phosphatidylcholine (EPC) was purchased from Avanti Polar Lipids (Alabaster, Ala.); cholesterol (Chol) from Calbiochem (San Diego, Calif.); N-Tris[hydroxymethyl]-2aminoethanesulfonic acid (TES) from Sigma; hydrogenated soy phosphatidylcholine (HSPC) from Natterman (Cologne, FRG); rhodamine-labeled phospholipids from Avanti; desferrioxamine mesylate (desferal) from Ciba-Geigy (Summit, N.J.); doxorubicin from Farmitalia, Carlo Erba (Milan, Italy) or Cetus (Emeryville, Calif.); and N-[4p-maleimidophenyl) butyryl]phosphatidylethanolamine (M-PE) from Molecular Probes (Portland, Oreg.). PEG ($M_r$ =1900)-derivatized phosphatidylethanolamine (PEG-PE) was synthesized as described (Allen et al., *Biochim. Biophys. Acta*, 1066: 29-36 (1991)), and obtained from Liposome Technology, Inc. (Menlo Park, Calif.).

B) Preparation of Fab' Fragments

Cloned rhuMAbHER2 sequences for heavy and light chain were co-expressed in *E. coli* as previously described (Carter et al., *Biotechnology* 10: 163-167 (1992)). The antibody fragment, rhuMAbHER2-Fab', was recovered from *E. coli* fermentation pastes by affinity chromatography with Streptococcal protein G (Carter et al., *Biotechnology*, 10:163-167 (1992) which is incorporated herein by reference), typically yielding Fab' with 60-90% containing reduced free thiol (Fab'-SH). As a control, an irrelevant humanized Fab' was used. Derived from an anti-CD 18 murine monoclonal antibody, rhuMAbH52-Fab' differs from rhuMAbHER2-Fab' only by replacement of the antigen-binding loops, and showed no detectable binding to any known murine or human antigen (Eigenbrot et al. *Proteins: Structure, Function, and Genetics*, 18: 49-62 (1994)).

C) Preparation of Liposomes

Liposomes were prepared according to the reverse phase evaporation method (Szoka & Papahadjopoulos, *Proc. Nat. Acad. Sci. USA*, 75: 4194-4198 (1978), with lipid composition including EPC:Chol (2:1) or, where stated, HSPC:Chol (3:2) and PEG-PE (0-6 mole %). Liposomes were subsequently extruded repeatedly under positive pressure with argon gas through polycarbonate membrane filters of defined pore size sequentially from 0.1 to 0.05 µm (Olson, et al., *Biochim. Biophys. Acta*, 55: 9-23 (1979); Szoka et al., *Biochem. Biophys. Acta*, 601: 559-571 (1980)). This procedure yields liposomes of 60-120 nm diameter as determined by dynamic light scattering. Liposome concentration was determined by phosphate assay (Bartlett, *J. Biol. Chem.*, 234: 466-468 (1959)). For immunoliposome preparations, 2 mole % M-PE (of total phospholipid) was included in the lipid mixture in chloroform prior to the making of liposomes (Martin and Papahadjopoulos, *J. Biol. Chem.*, 257: 286-288 (1982)). Liposomes without encapsulated doxorubicin were prepared in HEPES-NaCl buffer, pH 7.2, 300 mOsm. HSPC/Chol liposomes containing doxorubicin were prepared in 250 mM ammonium sulfate containing 1 mM desferal at pH 5.5. Unencapsulated ammonium sulfate was removed by gel filtration with G-75 Sephadex. Doxorubicin in powder form was then dissolved in this liposome suspension at 0.1 mg doxorubicin/µmole phospholipid (Papahadjopoulos et al., *Proc. Natl. Acad. Sci. USA*, 88: 11460-11464 (1991); Huang et al., *Cancer Res.*, 52:6774-6781 (1992)), which traps doxorubicin within the interior space of the liposome (Lasic et al., *FEBS Lett.*, 312: 255-258 (1992)). The efficiency of drug loading via salt gradient was high and reached >99% loading when 1 mg drug per 10 µmole phospholipid was used.

Fab' was conjugated to the liposomes after drug loading via thioether linkage, as previously described (Martin et al. *J. Biol. Chem.*, 257: 286-288 (1982). Since maleimide is more stable at lower pH, all procedures were performed at pH 5.5. Unreacted Fab' was separated from immunoliposomes by gel filtration with Sephacryl S-400. The maleimide group on immunoliposomes was deactivated after conjugation by 2-fold excess of mercaptoethanol to M-PE. The amount of Fab' conjugated was determined by BioRad protein assay.

Four types of liposomes were prepared. "Conventional" liposomes without antibody were composed of phosphatidylcholine and cholesterol only. "Sterically stabilized" liposomes additionally contained PEG-PE. Immunoliposomes were prepared by conjugation of the above with Fab' fragments derived from the humanized antibody rhuMAbHER2 to yield conventional or sterically stabilized immunoliposomes. Fab' fragments rather than intact antibody were used for the following reasons: 1) rhuMAbHER2-Fab' fragments can be expressed as recombinant proteins in *E. coli* at extremely high efficiency (Carter et al., supra.) the free thiol group in the Fab' hinge region provides a readily available site for covalent attachment to modified liposomes, and is distant from the antigen binding site; and 3) rhuMAbHER2-Fab' has far less antiproliferative activity than intact rhuMAbHER2, and thus it was of interest to see whether attachment of anti-p185$^{HER2}$-Fab' to liposomes would reconstitute this activity. Typically, conjugation resulted in approximately 50-100 Fab' molecules per liposome particle.

Example 2

Immunoliposome Binding

The ability of anti-p185$^{HER2}$ immunoliposomes to bind in vitro to breast cancer cells which overexpress the p185$^{HER2}$ receptor was evaluated by two methods; a flow cytometric assay and a competitive binding assay. For the flow cytometric assay, SK-BR-3, which express high levels of p185$^{HE2}$, or MCF-7 cells, were exposed to anti-p185$^{HER2}$ immunoliposomes for 45 minutes on ice, washed with PBS, stained with a secondary anti-human antibody to detect bound immunoliposomes (FITC-labeled goat anti-human IgG), washed with PBS again, and then subjected to flow cytometry (FIG. 1). SK-BR-3 cells bound significant amounts of either conventional or sterically stabilized anti-p185$^{HER2}$ immunoliposomes, but not control liposomes lacking Fab'. MCF-7 breast cancer cells, which do not overexpress p185$^{HER2}$, showed minimal binding to anti-p185$^{HER2}$, immunoliposomes (data not shown).

Figure 2:
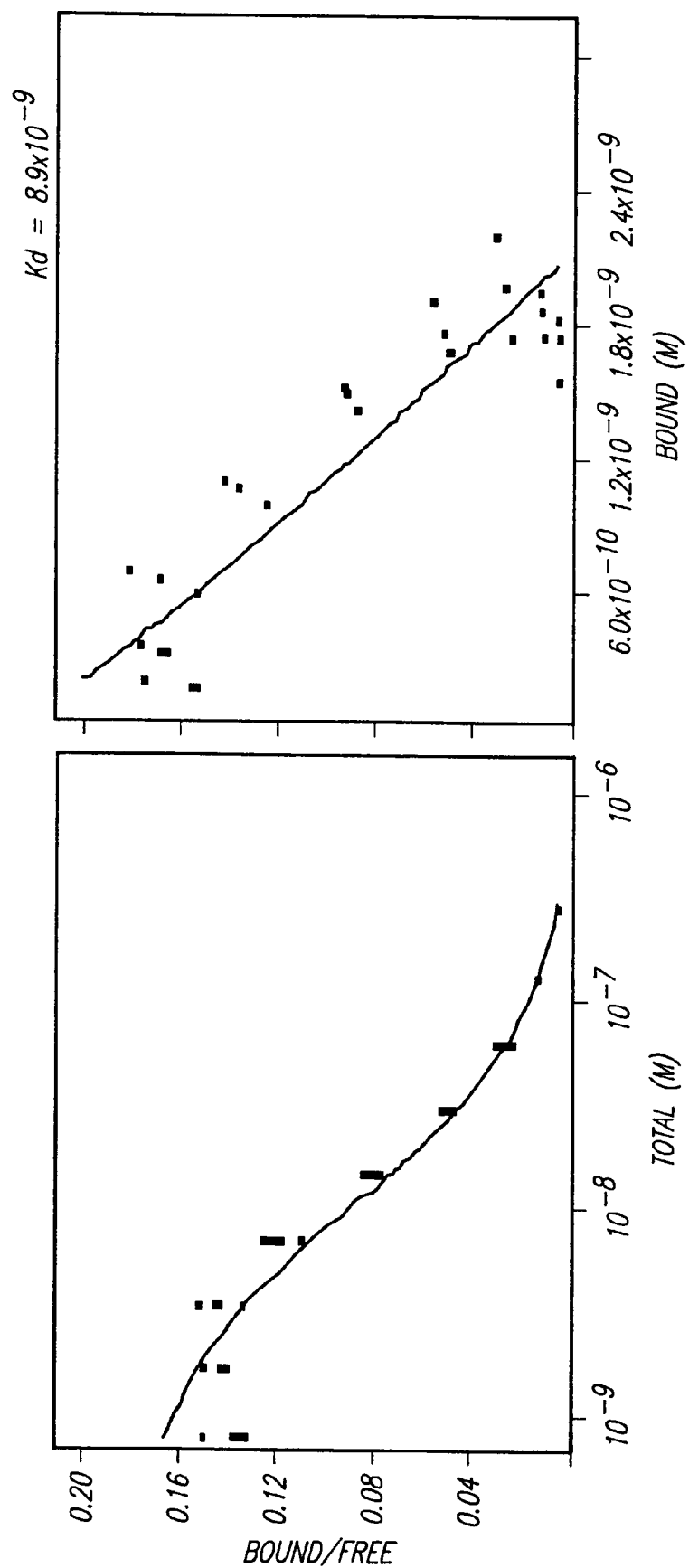
FIG. 2 shows the binding of anti-p185$^{HER2}$ conventional immunoliposomes to BT-474 cells. (A) BT-474 cells in monolayer culture were treated with conventional immunoliposomes in the presence of competing $^{125}$I-labeled rhuMAbHER2 as described in Methods. (B) Scatchard transformation of the data shown in (A).

Another measure of binding was afforded by a competitive binding assay, in which SK-BR-3 (breast cancer cells) or BT-474 cells in monolayer culture were simultaneously incubated with $^{125}$I-labeled rhuMAbHER2 or muMAb4D5, at 0.1 nM for 18 hours at 4° C., and increasing concentrations of anti-p185$^{HER2}$ immunoliposomes (FIG. 2). Counts bound were determined by gamma counting. Anti-p185$^{HER2}$2 immunoliposomes efficiently displaced binding of rhuMAbHER2 to both SK-BR-3 cells (data not shown) and BT-474 cells (which also express high levels of p185$^{HER2}$). An approximation of binding affinity was obtained via Scatchard analysis of the binding data, by making the assumption that Fab' on immunoliposomes behaved as free ligand. Using this model, apparent binding constants for the immunoliposomes were comparable to those of free (i.e. non-liposomal) rhuMAb-HER2-Fab1 or intact rhuMAbHER2. Conventional or sterically stabilized (6 mole % PEG-PE) control liposomes lacking Fab' showed negligible binding. A summary of the binding data is shown in Table 1.

TABLE 1

Binding of anti-P185$^{HER2}$ immunoliposomes to BT-474 cells.

| Ligand | Apparent K$_d$ (nM) | EC$_{50}$ (nM) |
|---|---|---|
| Control Liposome, Conventional | No displacement | >1000 |
| Control Liposome, Sterically Stabilized | 2500 | >1000 |

TABLE 1-continued

Binding of anti-P185$^{HER2}$ immunoliposomes to BT-474 cells.

| Ligand | Apparent K$_d$ (nM) | EC$_{50}$ (nM) |
|---|---|---|
| Anti-p185$^{HER2}$ Immunoliposome, Conventional | 9 | 15 |
| anti-p185$^{HER2}$ Immunoliposome, Sterically Stabilized | 58 | 78 |
| rhuMAbHER2-Fab' | 22 | 30 |
| rhuMAbHER2 | 1 | 2 |

Example 3

Anti-Proliferative Activity of "Growth-Inhibiting" Immunoliposomes

To test the antiproliferative activity of immunoliposomes alone, without encapsulated drugs, tumor cells such as SK-BR-3 or BT-474 cells were grown in monolayer culture and then incubated at 37° C. with varying concentrations of immunoliposomes based on antibody content. After continuous treatment for 4 days, cell monolayers were washed with PBS and stained with crystal violet dye (0.5% in methanol) for determination of relative proliferation as previously described (Hudziak, et al., *Mol. Cell Biol.* 9: 1165-1172 (1989)).

While intact (bivalent) rhuMAbHER2 inhibited the growth of p185$^{HER32}$-overexpressing breast cancer cells in monolayer culture, monovalent Fab' fragments of this antibody (rhuMAbHER2-Fab') are much less effective at inhibiting growth (O'Connell et al. pages 218-239 *In Protein Folding In Vivo and In Vitro.*, Cleland J L, ed. Washington, D.C., American Chemical Society, (1993)). This observation suggested that cross-linking of p185$^{HER2}$ receptors by bivalent antibody is important for the antiproliferative effect, and raised the question of whether liposomal anchoring of rhuMAbHER2-Fab' fragments might improve the antiproliferative activity of Fab' by increasing effective valency.

Figure 3:
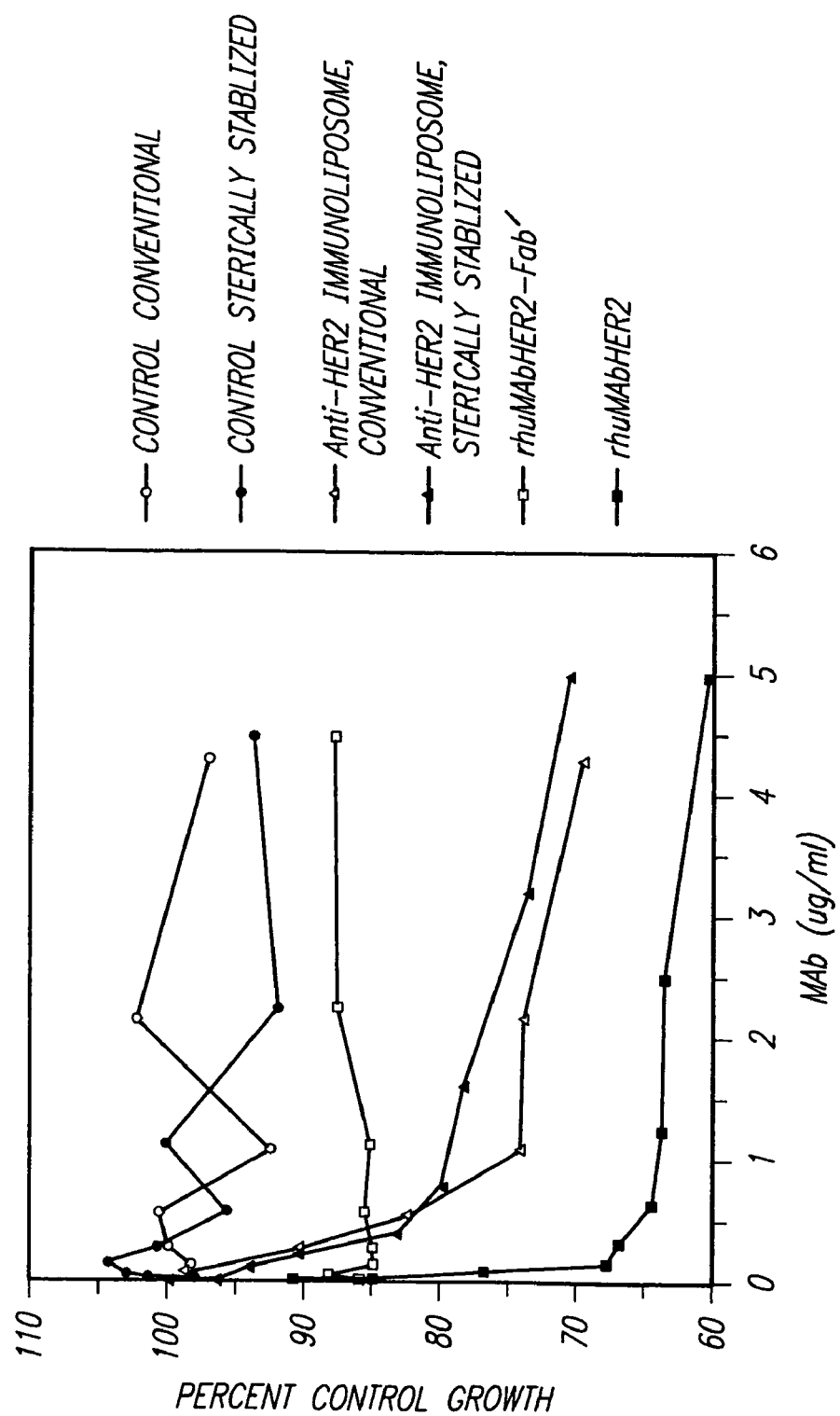
FIG. 3 illustrates the antiproliferative activity of anti-p185$^{HER2}$ immunoliposomes against SK-BR-3 cells. SK-BR-3 cells in monolayer culture were treated with immunoliposomes at antibody doses indicated on the abscissa, and relative cell proliferation determined as described in Methods. Control liposomes lacking antibody were dosed according to liposome concentration, and are plotted at equivalent liposome concentration with the appropriately matched immunoliposome. Control (no antibody) conventional liposomes; control sterically stabilized (6 mole % PEG-PE) liposomes; conventional immunoliposomes; anti-p$_{185}$$^{HER2}$ sterically stabilized (6 mole % PEG-PE) immunoliposomes; free (non-liposomal) rhuMAbHER2-Fab'; and free rhuMAbHER2 bivalent antibody are shown as indicated in the key.

The effect of anti-p185$^{HER2}$ immunoliposomes upon SK-BR-3 cells in monolayer culture was tested and compared to rhuMAbHER2 and rhuMAbHER2-Fab' (FIG. 3). Treatment with conventional or sterically stabilized control liposomes lacking Fab' did not significantly affect cell growth. In contrast, both conventional and sterically stabilized anti-p185$^{HER2}$ immunoliposomes inhibited growth in a dose-dependent manner. The growth inhibitory effect of the immunoliposomes reached a plateau of about 30% growth inhibition (70% of control growth), approaching the 40% growth inhibition seen with free intact rhuMAbHER2. In contrast, free rhuMAbHER2-Fab' induced only modest growth inhibition. Similar results were also obtained with p185$^{HER2}$-overexpressing BT-474 breast cancer cells (data not shown).

It is notable that liposome-associated rhuMAbHER2-Fab' produced a markedly greater antiproliferative effect than the same amount of rhuMAbHER2-Fab' free in solution. A plausible explanation is that liposomel anchoring of rhuMAb-HER2-Fab' allows cross-linking of p185$^{HER2}$, thus yielding biological activity which is comparable to that of the intact bivalent antibody.

Example 4

Cytotxicity of Anti-p185$^{HER2}$ Immunoliposomes Containing Doxorubicin

Although empty anti-p185$^{HER2}$ immunoliposomes displayed antiproliferative activity against p185$^{HER2}$-overexpressing breast cancer cells in culture, it was possible to greatly augment the antineoplastic effect of the immunoliposomes by loading them with cytotoxic agents, thus producing a targeted drug delivery system. Doxorubicin was used, because of preclinical and clinical evidence suggesting that doxorubicin may be particularly useful against breast cancers overexpressing $p185^{HER2}$, with or without concomitant immunotherapy. It was therefore of interest to evaluate the cytotoxicity and specificity of doxorubicin-loaded anti-$p_{185}^{HER2}$ immunoliposomes against $p185^{HER2}$-overexpressing breast cancer cells and against non-malignant cells that do not overexpress $p185^{HER2}$.

Because of the efficient internalization shown by $p185^{HER2}$ immunoliposomes (see Example 5), it was expected that the liposomes might be just as effective at killing $p185^{HER2}$-overexpressing breast cancer cells in culture as free doxorubicin, a small (MW 544) amphipathic molecule that readily passes through the cell membrane. On the other hand, cells which do not overexpress $p185^{HER2}$, while susceptible to free doxorubicin, would escape cytotoxic injury from doxorubicin-loaded anti-$p185^{HER2}$ immunoliposomes because of the inability of the immunoliposomes to target them.

To test the cytotoxicity of doxorubicin-loaded immunoliposomes, SK-BR-3 or WI-38 cells in monolayer culture were incubated with free doxorubicin or doxorubicin-loaded immunoliposomes for 1 hour, and then washed extensively with media. The cells were then further incubated at 37° C. for 3 days, after which cell number was estimated by crystal violet staining as described above. Comparison with other assays of cell growth including alamar blue staining, MTT staining, and direct cell counting yielded essentially the same results.

Figure 4A:
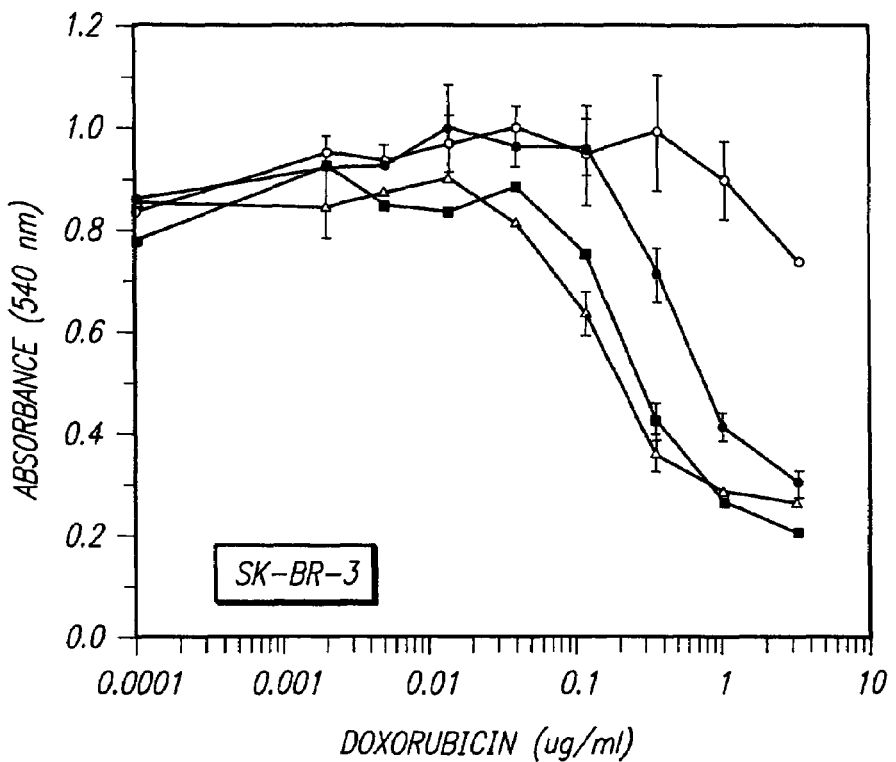
FIG. 4 shows the cytotoxicity of anti-p185$^{HER2}$ immunoliposomes containing doxorubicin. HSPC: Chol liposomes were loaded with doxorubicin as described in Methods. (A) SK-BR-3 cells. (B) WI-38 cells. Cells in culture were treated for 1 hour with: conventional immunoliposomes (triangles); sterically stabilized (2 mole % PEG-PE) immunoliposomes (closed circles); control (irrelevant antibody) sterically stabilized (2 mole % PEG-PE) immunoliposomes (open circles); or free doxorubicin alone (closed squares). Immunoliposomes contained 60-70 µg antibody/µmol phospholipid and 55-80 µg doxorubicin/µmol phospholipid; antibody/doxorubicin ratio was 0.8-1.2. Cells were counted 3 days after treatment as described in Methods.

The results of the SK-BR-3 cells treated for 1 hour with various doxorubicin-loaded immunoliposome preparations, are shown in FIG. 4. Under these conditions, the antiproliferative effect of rhuMAbHER2 is not apparent, as it requires continuous exposure of the cells to rhuMAbHER2 (Hudziak et al., *Mol. Cell Biol.*, 9: 1165-1172 (1989)). Treatment with free doxorubicin for 1 hour yielded significant cytotoxicity, with an $IC_{50}$ of approximately 0.3 μg/ml. Doxorubicin-loaded anti-$p_{185}^{HER2}$ immunoliposomes showed comparable dose-dependent cytotoxicity, with an $IC_{50}$ of approximately 0.2/cg/ml for conventional anti-$p185^{HER2}$ immunoliposomes and approximately 1.0 μg/ml for sterically stabilized (2 mole % PEG-PE) anti-$p185^{HER2}$ immunoliposomes. These results indicated that anti-$p185^{HER2}$ immunoliposome delivery of doxorubicin to $p185^{HER2}$-overexpressing cells in culture was as efficient a process as the rapid diffusion of free doxorubicin into the cells. Doxorubicin-loaded anti-$p185^{HER2}$ immunoliposomes were between 10- to 30-fold more cytotoxic than doxorubicin-loaded immunoliposomes bearing irrelevant Fab', which only affected cell growth at relatively high concentrations (>3.3 μg/ml).

Figure 4B:
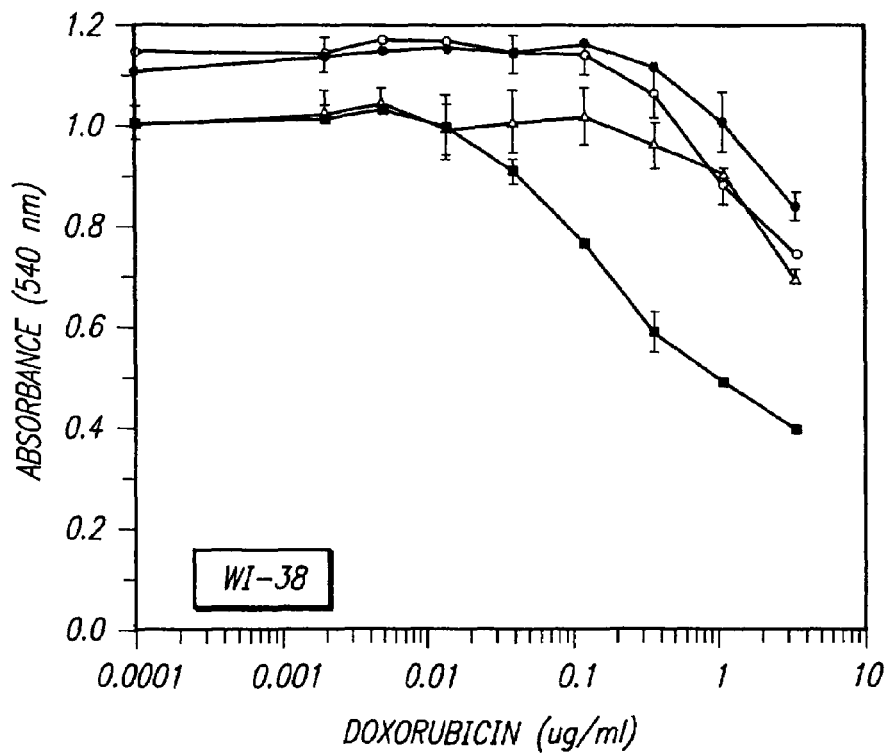

WI-38 cells, a non-malignant lung fibroblast cell line which expresses minimal levels of $p185^{HER2}$, were also treated with doxorubicin and with doxorubicin-loaded anti-$p185^{HER2}$ immunoliposomes (FIG. 4B). Free doxorubicin again produced significant dose-dependent cytotoxicity against WI-38 cells. However, doxorubicin-loaded anti-$p185^{HER2}$ immunoliposomes produced much reduced (20-fold less) cytotoxicity against these cells, and were indistinguishable from doxorubicin-loaded immunoliposomes bearing irrelevant Fab'. These results demonstrated the specificity of anti-$p185^{HER2}$ immunoliposome treatment for $p185^{HER2}$-overexpressing targets, and further confirmed that the cytotoxicity observed against SK-BR-3 cells was not simply due to leakage of doxorubicin out of anti-$p185^{HER2}$ immunoliposomes and into solution.

Example 5

Internalization of Immunoliposomes Into the Cytoplasm of the Target Cell

To assess internalization of immunoliposomes into the cytoplasm of the target cell by fluorescence microscopic assay, liposomes and immunoliposomes were prepared as described in Example 1 with the addition of rhodamine-phosphatidylethanolamine at 1 mole % of the phospholipid components. The resulting rhodamine labeled liposomes or immunoliposomes were incubated for varying amounts of time at 37° C. with SK-BR-3 cells grown to subconfluence on cover slips. The cells were then fixed with 3% paraformaldehyde, mounted in 90% glycerol/100 mM Tris, pH8.5, containing 0.1% p-phenylenediamine (Sigma) as an antibleaching reagent, and observed with a Leitz Aristoplan fluorescence microscope or a Molecular Dynamics Multi-Probe 2001 confocal microscope.

To assess internalization and intracellular disposition by electron microscopy, immunoliposomes were loaded with colloidal gold particles of 5-15 nm as previously described (Huang et al., *Cancer Res.*, 52: 5135-5143 (1992); Straubinger et al., *Cell*, 32: 10639-1079 (1983). Gold-containing immunoliposomes were incubated at 37° C. with SK-BR-3 cells grown on cover slips for varying amounts of time, and the cells were then fixed and processed for electron microscopy. Stabilization of liposomes was achieved using tannic acid in the primary fixation(Straubinger et al.,, supra), which provided adequate albeit not optimal preservation of the ultrastructure.

The antibody rhuMAbHER2 is rapidly internalized by $p185^{HER2}$-overexpressing tumor cells via receptor-mediated endocytosis (Sarup et al., *Growth Regul.* 1: 72-82 (1991)). To assess whether anti-$p185^{HER2}$ immunoliposomes are internalized within SK-BR-3 cells, cells were treated with rhodamine-labeled immunoliposomes for different time intervals, fixed and visualized by fluorescence microscopy. SK-BR-3 cells treated with conventional or sterically stabilized control liposomes lacking Fab' showed neither surface nor internal rhodamine fluorescence, consistent with the inability of control liposomes to bind to these cells. When treated with conventional anti-$p_{185}^{HER2}$ immunoliposomes, SK-BR-3 cells exhibited intense foci of fluorescence both at the cell surface and intracellularly within 30 minutes of treatment. Confocal fluorescence microscopy confirmed that rhodamine fluorescence was present both at the cell surface and internalized within the cytoplasm of SK-BR-3 cells. In contrast, treatment with sterically stabilized anti-$p185^{HER2}$ immunoliposomes containing high PEG-PE concentrations (6 mole %) resulted in minimal intracellular fluorescence after 30 minutes. Because it appeared that the presence of PEG-PE retarded immunoliposome internalization, sterically stabilized immunoliposomes containing reduced concentrations of PEG-PE were evaluated. Immunoliposomes containing 2 mole % PEG-PE yielded an intermediate degree of intracellular fluorescence after 30 minutes, i.e. less than that seen with conventional immunoliposomes but more than that seen with 6 mole % PEG-PE-containing immunoliposomes. Despite somewhat retarded internalization, the sterically stabilized immunoliposomes containing 2% PEG-PE did accumulate intracellularly with longer incubation time, such as at 2 hours. Thus, while anti-$p185^{HER2}$ immunoliposomes were internalized within SK-BR-3 cells, the rate of internalization was inversely related to the PEG-PE content of the immunoliposomes.

To study the intracellular disposition of immunoliposomes and their contents, electron microscopy was performed using immunoliposomes containing encapsulated colloidal gold particles. SK-BR-3 cells treated with conventional anti-p185$^{HER2}$ immunoliposomes for 30 minutes showed numerous gold-containing immunoliposomes bound at the cell surface and present intracellularly. Many immunoliposomes were observed contiguous with, and apparently bound to, the cell membrane. Some immunoliposomes were found in coated pits as well as within coated vesicles, endosomes, multivesicular bodies, and lysosomes. This intracellular distribution is consistent with internalization via the coated pit pathway. However, also observed were immunoliposomes appearing to fuse with the cell membrane, without coated pit formation. In addition, some gold particles appeared free within the cytoplasm, not associated with a liposomal capsule or a membrane-bound organelle. Gold particles free within the cytoplasm might have resulted from fusion events between immunoliposomes and the cell membrane. Alternatively, they may have arisen following endocytosis, with escape of the encapsulated gold particles occurring somewhere along the coated pit pathway.

Example 6

In Vivo Tumor Localization and Biodistribution of Immunoliposomes and Immunoliposome Contents Young (4-6 week) female SCID mice were injected with BT-474 cells in the subcutaneous tissue of the flank or of the mammary fat pad, and additionally treated with subcutaneously implanted estrogen pellets to support the tumorigenic growth of these cells. When palpable tumors achieved a size of at least 300 mm$^3$ (typically 14 days post-inoculation), immunoliposomes were administered by single intravenous injection (via tail vein) or single intraperitoneal injection, in a volume of approximately 200 μL containing approximately I μmole of total lipid. Animals were sacrificed at designated times post-injection, organs perfused with saline in situ, and tissues immediately excised for analysis. For biodistribution and imaging analysis after injection of rhodamine-labeled immunoliposomes, freshly excised tissues were fixed and examined by confocal fluorescence microscopy. For quantitative localization of doxorubicin delivered by immunoliposomes, excised tissues were homogenized and subjected to acidified ethanol extraction; the extracted doxorubicin was then measured by spectrofluorimetric assay as previously described (Gabizon et al., *J. Natl. Cancer Inst.*, 81: 1484-1488 (1989)).

The biodistribution of anti-p185$^{HER2}$ immunoliposomes and their ability to localize to and accumulate within tumors in vivo was evaluated in a tumor xenograft model. In this model, immunodeficient mice carrying established subcutaneous BT-474 tumor xenografts were treated with immunoliposomes by a single intravenous or intraperitoneal injection. Imaging studies with confocal fluorescence microscopy were performed to detect rhodamine-labeled immunoliposomes within various tissues of animals sacrificed after treatment. Within 6 hours of intravenous injection, rhodamine fluorescence was visualized within the xenografted tumor, while no significant fluorescence was observed within surrounding muscle. This technique, however, did not allow precise delineation of immunoliposomes within tumor tissue. For a quantitative evaluation of the biodistribution and localization of doxorubicin delivered by immunoliposomes, doxorubicin was assayed from tissue extracts of treated animals. 24 hours after intraperitoneal injection, doxorubicin delivered by sterically stabilized anti-p185$^{HER2}$ immunoliposomes had accumulated within tumor xenografts, with lower levels of doxorubicin found in surrounding muscle and in blood (Table 2).

TABLE 2

Anti-P185$^{HER2}$ immunoliposome delivery of doxorubicin in vivo: biodistribution 24, hrs after single ip injection.

| Tissue/Fluid | Doxorubicin Level (% injected dose/g of tissue) |
| --- | --- |
| Tumor | 1.64 |
| Muscle | 0.61 |
| Liver | 13.46 |
| Ventricular Blood | 0.88 |
| Tumor/Muscle Ratio | 2.69 |
| Tumor/Blood Ratio | 1.88 |

Example 7

Preparation of Immunoliposomes Bearing Fab' on PEG

To improve the specific targeting and internalization of the immunoliposomes of this invention tumor specific Fab' fragments (rhuMAbHER2-Fab') were conjugated to distal ends of lilposome-grafted polyethylene glycol chains via sulfhydryl reactive maleimide groups. To provide the linker group (maleimide) for reacting with SH fo Fab', α-distearoylphosphatidylethanolaminocarbonyl-ω-malimidopropionylamidopolyethylene glycol was synthesized from distearoylphosphatidylethanolamine and heterobifunctional PEG derivative (N-hydroxysuccinimidyl-PEG-maleimide) according to standard methods. The maleimidederivitive of PEG-PE was included in the liposome preparation as described above and the Fab' fragment was conjugated with the liposome via the sulfhydryl group at pH 7.2.

Liposome composition was as described above, except that M-PE was eliminated as it was no longer required for linkage of the antibody fragment. Typically PEG (PEG-PE) ranged from about 10 to about 12 mole percent of total phospholipid and Fab' conjugated PEG-derivatized lipid ranged from about 0.6 mole percent to about 1 mole percent of total lipid.

In the culture of HER-overexperssing breast cancer cells, such anti-HER2 sterically stabilized liposomes had the same binding and internalization effeciency independent of the amount of polyethylene glycol-modified phospholipid.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. An immunoliposome that is internalized into a cell bearing a growth factor receptor on its cell surface, said immunoliposome comprising:
    a hydrophilic polymer derivatized lipid;
    a recombinantly produced antibody fragment specifically binding to the receptor on the cell surface said fragment attached to the hydrophilic polymer of the derivatized lipid; and,
    an amphipathic vesicle-forming lipid, said vesicle-forming lipid forming a liposome; and, wherein when said immunoliposome is contacted with said cell bearing a growth factor receptor on its cell surface, said immunoliposome is internalized into the cell and where the growth factor receptor is selected from the group consisting of HER1 and HER2.

2. The immunoliposome of claim 1, wherein the antibody fragment is a Fab'.

3. The immunoliposome of claim 1 wherein the antibody fragment is a humanized Fab' domain of a monoclonal antibody.

4. The immunoliposome of claim 1, wherein said vesicle forming lipid is selected from the group consisting of a phospholipid, a glycolipid, a sphingolipid, and a sterol.

5. The immunoliposome of claim 1 wherein the hydrophilic polymer is polyethylene glycol.

6. An immunoliposome that is internalized into a cell bearing a HER 1 growth factor receptor on its cell surface, said immunoliposome comprising:
   a hydrophilic polymer derivatized lipid;
   a recombinantly produced antibody fragment specifically binding to the HER1 receptor on the cell surface said fragment attached to the hydrophilic polymer of the derivatized lipid; and,
   an amphipathic vesicle-forming lipid, said vesicle-forming lipid forming a liposome; and, wherein when said immunoliposome is contacted with said cell bearing a growth factor receptor on its cell surface, said immunoliposome is internalized into the cell.

7. The immunoliposome of claim 6 wherein the antibody fragment is a Fab'.

8. The immunoliposome of claim 6 wherein the antibody fragment is a humanized Fab' domain of a monoclonal antibody.

9. The immunoliposome of claim 6 wherein said vesicle forming lipid is selected from the group consisting of a phospholipid, a glycolipid, a sphingolipid, and a sterol.

10. The immunoliposome of claim 6 wherein the hydrophilic polymer is polyethylene glycol.

* * * * *